US011163056B2

(12) United States Patent
Viberg et al.

(10) Patent No.: US 11,163,056 B2
(45) Date of Patent: Nov. 2, 2021

(54) RADAR DETECTOR FOR MONITORING OF BODILY FUNCTIONS

(71) Applicant: RAYTELLIGENCE AB, Halmstad (SE)

(72) Inventors: Per-Arne Viberg, Halmstad (SE); Emil Nilsson, Harplinge (SE)

(73) Assignee: RAYTELLIGENCE AB, Halmstad (SE)

( * ) Notice: Subject to any disclaimer, the term of this patent is extended or adjusted under 35 U.S.C. 154(b) by 347 days.

(21) Appl. No.: 15/781,594

(22) PCT Filed: Dec. 9, 2016

(86) PCT No.: PCT/SE2016/051236
§ 371 (c)(1),
(2) Date: Jun. 5, 2018

(87) PCT Pub. No.: WO2017/099661
PCT Pub. Date: Jun. 15, 2017

(65) Prior Publication Data
US 2020/0264299 A1  Aug. 20, 2020

(30) Foreign Application Priority Data

Dec. 10, 2015 (SE) .................................... 1551621-4
Oct. 28, 2016 (SE) .................................... 1651423-4

(51) Int. Cl.
*G01S 13/88* (2006.01)
*A61B 5/024* (2006.01)
(Continued)

(52) U.S. Cl.
CPC .......... *G01S 13/88* (2013.01); *A61B 5/02444* (2013.01); *A61B 5/0507* (2013.01);
(Continued)

(58) Field of Classification Search
CPC ......... A61B 5/0507; A61B 5/024; A61B 5/05; A61B 5/0022; A61B 5/1114; A61B 5/7221
See application file for complete search history.

(56) References Cited

U.S. PATENT DOCUMENTS 7,567,200 B1   7/2009  Osterweil
7,916,066 B1   3/2011  Osterweil
(Continued)

FOREIGN PATENT DOCUMENTS

JP    2013092512    5/2013
WO   WO2015/174879   11/2015

OTHER PUBLICATIONS

International Search Reporton corresponding PCT application (PCT/EP2016/051236) from International Searching Authority (SE) dated Apr. 25, 2017.
(Continued)

*Primary Examiner* — Timothy X Pham
(74) *Attorney, Agent, or Firm* — Klein, O'Neill & Singh, LLP

(57) ABSTRACT

A detector (210) for indicating bodily functions of a person in the surroundings of the detector (210) is proposed. The detector (210) comprises a support structure and a Continuous-Wave (CW) radar module (214) supported by the support structure. The radar module (214) is configured to emit microwaves and receive microwaves that have been reflected in the surroundings of the detector (210), wherein the radar module (214) is configured to determine data indicating bodily functions from microwaves reflected on a person. The detector (210) further comprises a collimator (216) supported by the support structure and configured for collimating the emitted microwaves in one spatial direction, or towards a plane.

13 Claims, 12 Drawing Sheets

(51) Int. Cl.
*A61B 5/0507* (2021.01)
*A61B 5/08* (2006.01)
*A61B 5/11* (2006.01)
*G01S 13/02* (2006.01)
*F21K 9/232* (2016.01)

(52) U.S. Cl.
CPC .............. *A61B 5/0816* (2013.01); *A61B 5/11* (2013.01); *G01S 13/02* (2013.01); *A61B 2560/0406* (2013.01); *F21K 9/232* (2016.08)

(56) References Cited

U.S. PATENT DOCUMENTS

| | | | |
|---|---|---|---|
| 10,539,396 B1* | 1/2020 | Plunk | H01Q 21/064 |
| 2008/0077015 A1 | 3/2008 | Boric-Lubecke et al. | |
| 2009/0227882 A1 | 9/2009 | Foo | |
| 2010/0130873 A1 | 5/2010 | Yuen et al. | |
| 2010/0241009 A1* | 9/2010 | Petkie | A61B 5/024 |
| | | | 600/484 |
| 2010/0309454 A1* | 12/2010 | Zhang | G01J 3/28 |
| | | | 356/39 |
| 2012/0081266 A1* | 4/2012 | Graber | H01Q 19/17 |
| | | | 343/912 |
| 2013/0002434 A1 | 1/2013 | Cuddihy et al. | |
| 2013/0082598 A1 | 4/2013 | Csato et al. | |
| 2013/0135137 A1 | 5/2013 | Mulder et al. | |
| 2013/0194126 A1 | 8/2013 | Paoletti | |
| 2014/0058256 A1 | 2/2014 | De Jong | |
| 2014/0155729 A1 | 6/2014 | Saitoh | |
| 2014/0231649 A1* | 8/2014 | Zhao | G01J 3/0237 |
| | | | 250/339.11 |
| 2014/0316261 A1 | 10/2014 | Lux et al. | |
| 2014/0324382 A1 | 10/2014 | Greene et al. | |
| 2015/0378165 A1* | 12/2015 | Zheng | G02B 27/0179 |
| | | | 359/633 |
| 2016/0238375 A1* | 8/2016 | Hochrein | G01B 11/06 |
| 2017/0322431 A1* | 11/2017 | Wang | G02F 1/0126 |
| 2018/0164489 A1* | 6/2018 | Fattal | G02B 6/0058 |

OTHER PUBLICATIONS

Written Opinion on corresponding PCT application (PCT/ EP2016/ 051236) from International Searching Authority (SE) dated Apr. 25, 2017.
Petkie et al.; "Remote respiration and heart rate monitoring with millimeter-wave/terahertz radars"; Proceedings of the SPIE—The International Society of Optical Engineering, 2008, vol. 7117; whole document.

\* cited by examiner

RADAR DETECTOR FOR MONITORING OF BODILY FUNCTIONS

CROSS-REFERENCE TO RELATED APPLICATION

This application is the National Phase, under 35 U.S.C. § 371(c), of International Application No. PCT/SE2016/051236, filed Dec. 9, 2016, which claims priority from SE 1551621-4, filed Dec. 10, 2015, and SE 1651423-4, filed Oct. 28, 2016. The disclosures of all of the referenced applications are incorporated herein by reference in their entireties.

FEDERALLY SPONSORED RESEARCH OR DEVELOPMENT

Not Applicable

TECHNICAL FIELD

The invention relates to detectors for remotely monitoring of bodily functions.

BACKGROUND ART

In many healthcare situations, the ability to monitor and detect bodily functions or vital life signs, such as heart beats, are of great importance. There are systems based on wearable devices that are attached to the body, such as watches, wrist bands, or integrated sensors in clothing. These systems have the drawbacks that they need to be carried and require batteries. Thus, there is a need for monitoring systems that do not need to be carried and that can be powered by mains electricity.

Ultra-WideBand (UWB) impulse-radar systems have been used to remotely monitor vital life signs and bodily functions. These systems operate by means of sending short pulses, such as 100 picosecond pulses, and receiving the echo from objects in the environment. The short pulses causes the output signal to spread out over a wide frequency band in the radio spectrum. Typically, this could be in a band from 1 GHz to 6 GHz. Thus, these systems are subject to interference with other technologies allocated within the same frequency band, such as Global Positioning System, TV, Wireless Local Area Network, and military radio equipment. Thus, these UWB impulse-radar systems are allowed to operate only at low energies to avoid interference. This typically leads to limited spatial ranges and weak signals. Further, there is a tradeoff between sampling frequency and position accuracy of the target, which in turn means a limited performance of a UWB impulse-radar systems. Further, the short pulses are also very hard to generate in a controlled and consistent manner, and the spread in the spectrum may vary between pulses in the UWB impulse-radar system.

The abovementioned monitoring systems typically require cabling for power supply, which complicates the setting up and limits the placement of the systems. Further, the efficiency can typically be improved if the systems are installed close to the person being monitored, or if they have a coverage that is likely to cover the person being monitored. However, the abovementioned monitoring systems are typically limited to mountings on walls ceilings, where electric contacts typically are not readily available and manual adjustments are difficult.

SUMMARY

It is an object of the invention to overcome, or at least partly overcome, one or more of the above-identified limitations of the prior art. In particular, it is an object to improve the spatial accuracy and resolution in remote detection of bodily functions. It is also an object to improve the sensitivity in remote detection of bodily functions. It is a further object to provide high-sensitivity detectors or detector systems that are small and flexible with respect to placement.

To solve these objects, a detector for indicating, or monitoring, bodily functions of a person in the surroundings of the detector is provided. The detector comprises: a support structure and a Continuous-Wave (CW) radar module supported by the support structure. The radar module is configured to emit microwaves and receive, or detect, microwaves that have been reflected, or echoed, in the surroundings of the detector, wherein the radar module is configured to determine data indicating bodily functions from microwaves reflected at, on, or proximal to a person.

The detector may further comprise: a wireless communication circuit operationally connected to the radar module and configured to transmit a signal indicating data determined by the radar module. Further features of the detector are described below.

The CW radar module allows for microwaves within a specific open band, thus, the risk of interference is reduced and a stronger signal can be used, which improves the Signal-to-Noise ratio (S/N)) as compared to the UWB impulse-radar systems, which in turn means an improved sensitivity. CW microwaves are here understood to encompass both unmodulated and frequency-modulated CW radar. Bodily functions are understood to encompass one or more of heart activity, breathing, and limb movements. Data indicating bodily functions is understood to encompass data indicating changes in position or orientation of a surface of a body.

To solve the above objects, a lamp is also provided for being mounted in a light-fixture for light-bulbs and for indicating, or monitoring, bodily functions of a person. Here, the light-fixture comprises a socket for supporting a light-bulb and providing an electrical connection to the light-bulb. The lamp comprises: a base, or lamp cap, configured to be supported by the socket, wherein the base comprises an electric contact for establishing an electric connection with the socket. The lamp also comprises: a light-emitter configured for illuminating the surroundings of the lamp, and a detector for indicating bodily functions of a person in the surroundings of the detector. The detector of the lamp may comprise any of the features of the detector described herein.

The above described lamps allows for a placement of the detector at a location where a light-fixture is situated. This allows for the detector to be placed away from the ceiling and walls of a room and closer to its occupants. For example, the light-fixture may be in a table lamp or a floor lamp. Lamps, such as ceiling and wall mounted lamps, are typically placed so that they can illuminate beds or the like where people spend significant amounts of time. The installation of the detector is therefore simplified by a mounting in such a light-fixture. Additionally, light-fixtures for main lighting in smaller rooms are typically mounted in the ceiling at a location where it covers a significant portion of the room. Thus, a great coverage can easily be achieved by mounting a detector in this kind of light-fixtures.

The microwaves may have or comprise a radar frequency in the 24.125 GHz Industrial, Scientific and Medical (ISM) band, the 61.250 GHz ISM band, or the 122.500 GHz ISM band. Additionally or alternatively, the microwaves may have or comprise a radar frequency in the range 20 to 29 GHz, 22 to 27 GHz, and/or 24 to 25 GHz, or in the range 57 to 66 GHz, 59 to 64 GHz, and/or 61 to 62 GHz, or in the range 118 to 127 GHz, 120 to 125 GHz, and/or 122 to 123 GHz. These higher frequencies have a limited penetration, which makes them suitable for placement in direct line-of sight of the person to be monitored, which is enabled by the above described lamp that comprises detector. Additionally, these frequencies allows for a collimator of the microwaves that is of a suitable size for lamps used in common light-fixtures.

The radar module of the detector may be configured to determine the data indicating bodily functions by Doppler radar. Alternatively or additionally, the radar module of the detector may be configured to determine the data indicating bodily functions by frequency-modulated carrier-wave radar. The radar module may comprise a processor and a non volatile memory comprising program code instructions, that, when executed by the processor, causes the processor to operate the radar module and determine the data indicating bodily functions from microwaves reflected at the person. The data may correspond to an amplitude diagram indicating heart beats and/or breathing of the person.

In addition to determining data indicating bodily functions from microwaves reflected at a person, the radar module may be further configured to determine data indicating a position of the person. The frequency-modulated carrier-wave radar may be configured to determine data indicating the position. It may be configured to transmit microwaves in a sweep within a frequency interval, such as a chirp function from 57 GHz to 64 GHz. The duration of the sweep may vary from 1 ms to 100 ms. The radar module may comprise a mixing stage configured to generate a beat frequency of the received, or echoed, microwaves, and the data indicating the position may be determined from the beat frequency, for example via a Fast Fourier Transform (FFT).

The radar module of the detector may comprise a phased array antenna configured to reinforce a radiation pattern of the emitted microwaves in a first direction. This has the effect of an increased S/N, which means an improved sensitivity, and improved resolution in the first direction. The phased array antenna may be configured to allow an adjustment of the first direction. This allows for a flexibility in the placing of the detector or lamp around a desired spot that is to be monitored, which makes the setup easier.

The radar module of the detector may be configured to radiate microwaves at maximum power in a first direction. Additionally, the radar module of the detector may further be configured to receive microwaves at maximum power gain from the first direction. Additionally, or alternatively, the radar module of the detector may comprise a directional antenna for transmitting and receiving the microwaves. The directional antenna may be a high-gain antenna. For example, the high-gain antenna may be a parabolic antenna. These features have the effect of an increased S/N of the detector.

The radar module may comprise a plurality of antennas. The antennas may be spaced apart and jointly operate for allowing the data indicating the bodily functions and/or a position of the person. An antenna of the plurality of antennas may be configured to operate as a frequency-modulated carrier-wave radar, and another antenna of the plurality of antennas may be configured to operate as a Doppler radar. An antenna of the plurality of antennas may be configured to operate within a first frequency band, such as 20 to 29 GHz, and another antenna may be configured to operate in a second frequency band, such as 57 to 66 GHz.

The detector may further comprise a collimator for adjusting the spread of, or collimating, the microwaves that are emitted by the radar module to be, or become, more aligned with a first direction. The collimator may comprise a lens or a collimating lens. The lens may be a focusing lens configured to focus microwaves that have been reflected, or echoed, in the surroundings of the detector. The lens may have an inner convex surface facing the radar module and a planar outer surface facing away from the radar module. A lens is here understood to encompass a plurality lenses configured for adjusting the spread of, or collimating, the microwaves that are emitted by the radar module. The focal length may be between 0.01 m and 0.06 m, 0.02 m and 0.05 m, or 0.03 m, 0.04 m, and/or between 0.01 m to 0.02 m, 0.02 m to 0.03 m, 0.03 m to 0.04 m, 0.04 m to 0.05 m, or 0.05 m to 0.06 m. These features contribute to an increased S/N of the detector.

The collimator may comprise a diffraction grating or diffraction lens configured to generate microwave lobes of constructive interference in a plurality of directions simultaneously. The collimator, or lens, may comprise a metamaterial with negative refractive index.

The lens may be fixed relative to the radar module and the support structure may be configured to allow the orientation of the radar module to be changed. This allows for a more flexible detector with respect to placement. The detector, and/or the lamp, may be configured to allow the orientation of the radar module to be changed manually. A lamp with this feature is particularly advantageous, since it can typically be installed where it is easily accessible, such as in a table or desk lamp. Additionally or alternatively, the detector may further comprise: a first actuator configured to change the orientation of the radar module.

The detector may comprise a reflector for directing the microwaves in a first direction. The reflector may be composed of a metal, or comprise a sheet of metal.

The reflector may be planar and the collimator may be positioned between the radar module, or antenna, and the reflector. Alternatively, the reflector may be configured for adjusting the spread of, or collimating, the microwaves that are emitted by the radar module, or antenna, to be, or become, more aligned with the first direction. The reflector may be shaped as a portion of a paraboloid, a sphere, a parabolic cylinder, or a circular cylinder. The above features allow for a compact detector with a directed detection, which allows for a more flexible installment. The compact detector also allows for a more compact lamp, which allows for application in smaller standards of lamps and light-fixtures.

The orientation of the reflector may be adjustable relative to the radar module. This allows for a more flexible detector with respect to placement. The detector, and/or lamp, may further be configured to allow the orientation of the reflector to be changed manually. The detector may further comprise: a second actuator configured to change the orientation of the reflector.

The wireless communication circuit in the detector may be supported by the support structure. This allows for a more compact detector or lamp.

The lamp may further comprise: a power converter coupled to the electric contact and configured to supply the light-emitter, and the detector with electrical power. The power converter may be configured to receive mains electricity, such as 230 V AC at 50 Hz, or 120 V AC at 60 Hz. Alternatively, it may be configured to receive direct current electricity, such as 6V, 12 V or 24 V DC. Thus, no external transformer is typically required, which contributed to an easier setup.

The lens of the detector may be of an optically translucent or transparent material. Further, if the detector is fitted in a lamp, it may be configured to allow light from the light-emitter to pass through the lens and illuminate the surroundings of the lamp. The translucency or transparency allows for the light emitter to be positioned on the inside of the lens, and the emitted light to pass through the lens, which allows for a more compact lamp. This is particularly advantageous if the lens is supported by a transparent or translucent bulb of the lamp. Here, the lens may have a form and position, or be configured, so that it does not collimate light emitted from the light emitter. The lamp may extend in a second direction from the base, normal to the base, or along the symmetry axis of the base. The first direction may be at an angle to the second direction, and the support structure may be configured to allow a rotation of the radar module relative to the base. This also allows for a more compact lamp.

The light-emitter of the lamp may be configured to project light in the first direction for forming an illuminated area or pattern of varying brightness indicating the first direction. The area or pattern may comprise a bright or dark spot indicating the first direction. This allows for an accurate determination of the first directions, which may contribute to an improved S/N.

The lamp may comprise a first manual switch for switching on and off the detector or the radar module. Additionally or alternatively, the lamp may comprise a second manual switch for switching on and off the light-emitter. This allows for the light-emitter and the radar module to be switched on and off independently from one another. Thus, the detector of the lamp may be operational with the light switched off, and vice versa.

The lamp may comprise a bulb, or cover, of a material that is transparent and/or translucent to optical light and microwaves. The bulb may cover, enclose, partly enclose, or prevent manual access to the light emitter and/or the radar module. The bulb may be connected to and supported by the base or support structure. The bulb may be releasably attached to the base or support structure. The bulb may support the collimator. Alternatively, the support structure may support the lens.

The base, light-emitter, and detector of the lamp, the bulb, or the lamp as such, may be configured to fit in a light-fixture for general-service light-bulbs. For example, the fixture may be for 120 V in the sizes A17, A19 or A21, or for 230 V in the sizes A55 or A60. The base, light-emitter, and detector, or the lamp as such, may be configured to fit in a light-fixture for reflector light-bulbs. For example, the fixture may be for 120 V in the sizes R16, R20, R25 or R30, or for 230 V in the sizes R50, R63, R80 or R95. The base, light-emitter, and detector, or lamp as such, may be configured to fit in a light-fixture for parabolic aluminized reflector light-bulbs. For example, the fixture may be for 120 V in the sizes PAR16, PAR20, PAR30, PAR38, PAR 56 or PAR64, or for 230 V in the sizes PAR16, PAR20, PAR30, PAR38, PAR56 or PAR64.

The base may be configured to connect with an Edison screw socket, such as E11, E14, E27, and E40 used in Europe, or to connect with a bayonet mount or bayonet connector, such as BA15s, BA20d, B22d, GU10, and GZ10 type mounts, or to connect with a bi-pin connector, such as a G4, GU4, G8, and GU10 type connectors.

The detector may further comprise a collimator supported by the support structure and configured for collimating, limiting the spread of, or reducing the spread of, the emitted microwaves in one spatial direction. Alternatively, the detector may further comprise a collimator supported by the support structure and configured for collimating, limiting the spread of, or reducing the spread of, the emitted microwaves towards a plane. The collimation contributes to an improved detector sensitivity and the spatial accuracy close to the plane.

The radar module may comprise an antenna module for emitting and receiving, or intercepting, microwaves and the collimator may comprise an refractive body of a material that is refractive to the microwaves, wherein the refractive body constitutes a portion of a ring having an inner side and an outer side, and wherein the refractive body is positioned in front of the antenna module with its inner side facing the antenna module. The inner side and/or the outer side of the portion of the ring may define a circular arc. The refractive body may constitute a portion of a ring having a transverse, or radial, cross-section with a convex inner side facing the antenna module. Transverse is here understood to encompass any cross-section formed by a cut similar to a cut forming equal portions of a ring from a complete ring, or a radial cut in the case of a circular ring. These features allow for a compact detector that can emit microwaves that are collimated towards a plane, or propagating parallel to a plane, as compared to the size of a phased array antenna generating the corresponding collimated microwaves.

The convex inner side may have curvature, or a radius of curvature, that varies along the portion of the ring, or between the ends of the portion of the ring. This allows for a collimation of the microwaves that depends on the direction with respect to the module. The curvature may be smaller, or the radius of curvature greater, at the ends of the portion of the ring than at the middle of the portion of the ring. This generally has the effect that the microwaves are more collimated in a direction normal to the antenna module than to the sides. The refractive body constituting a portion of a ring may have a transverse, or radial, cross-section with a straight outer side facing away from the antenna module.

The refractive body constituting a portion of a ring, the inner side, or the outer side may correspond, or define, an arc subtending an angle in the range 80° to 200°, 90° to 180°, or 100° to 160°. This has the advantage of a wide coverage of the detector.

The antenna module may comprise a first receiving antenna and a second receiving antenna for intercepting microwaves that have been reflected in the surroundings of the detector, wherein the first receiving antenna is spaced apart from the second receiving antenna. The refractive body constituting a sector of a ring may be aligned with the first receiving antenna and the second receiving antenna. The radar module may further be configured to determine the distance and the location of the person with respect to the detector. This has the advantage that bodily functions of a person can be determined even though other persons are within the coverage of the detector.

The refractive body may be composed of a polymer material or a plastic material, such as PolyLactic Acid (PLA) and Acrylonitrile Butadiene Styrene (ABS).

One or more of the above objects are also achieved by a detector system for indicating bodily functions of a person in a room. The detector system comprises: a first detector and a second detectors. Each of the first detector and the second detector may have any of the features detector described above. The first detector and the second detector may be positioned at different heights in the room, and the collimator of the first detector and the collimator of the second detector may collimate, or limit the spread of, or reduce the spread of, the emitted microwaves in the same spatial direction, or towards a first plane and a second plane, respectively, wherein the first plane and the second plane are parallel. This has the effect of an improved spatial accuracy and an improved sensitivity in the two planes.

The collimator of the first detector and the collimator of the second detector may further be oriented to collimate, or limit the spread, of the microwaves in a vertical direction, or towards first horizontal plane and a second horizontal plane, respectively. Additionally or alternatively, the first detector and the second detector may be positioned at different heights in the room. This allows for a simultaneous monitoring at different heights, or levels, in the room, for example at floor level and at the level of a bed. This contributes to an improved likelihood of receiving a good signal from a person in the room, which in turn means an improved sensitivity of the system.

The first detector and the second detector may be aligned in a vertical direction and the antenna module of the first detector and the antenna module of the second detector may face the same direction. The detector system may further comprise: a detector support for supporting the first detector and the second detector in the room. The detector support may comprise a straight rail supporting the first detector and the second detector. The positions of the first detector and the second detector may be adjustable along the rail. The rail may comprise an electrical conduit, the first detector may comprise a first electrical connector operationally connected to the electrical conduit for allowing electric power to be supplied to the first detector, and the second detector may comprise a second electrical connector operationally connected to the electrical conduit for allowing electric power to be supplied to the second detector. These features contribute to a detector system that is easy to install, that provides a good coverage of the room, and that is compact. The detector support may further be configured for mounting the rail on a wall, or on a base or stand for being placed on the floor of the room. These features contribute to a compact system that is flexible with respect to the placement of the detectors.

The first detector may be positioned between 0.1 m and 1 m from the floor of the room and the second detector may be positioned between 1 m and 2 m from the floor of the room. It has been shown that his positioning is favorable in hospital environments and in geriatric care.

A detector and lamp for indicating bodily functions of a mammal, such as a horse or a dog. The detector and lamp may comprise any of the features described for the detector and lamp above, but all configured to function on a mammal instead.

Still other objectives, features, aspects and advantages of the invention will appear from the following detailed description as well as from the drawings.

BRIEF DESCRIPTION OF THE DRAWINGS

Embodiments of the invention will now be described, by way of example, with reference to the accompanying schematic drawings, in which.

DETAILED DESCRIPTION

Figure 1A:
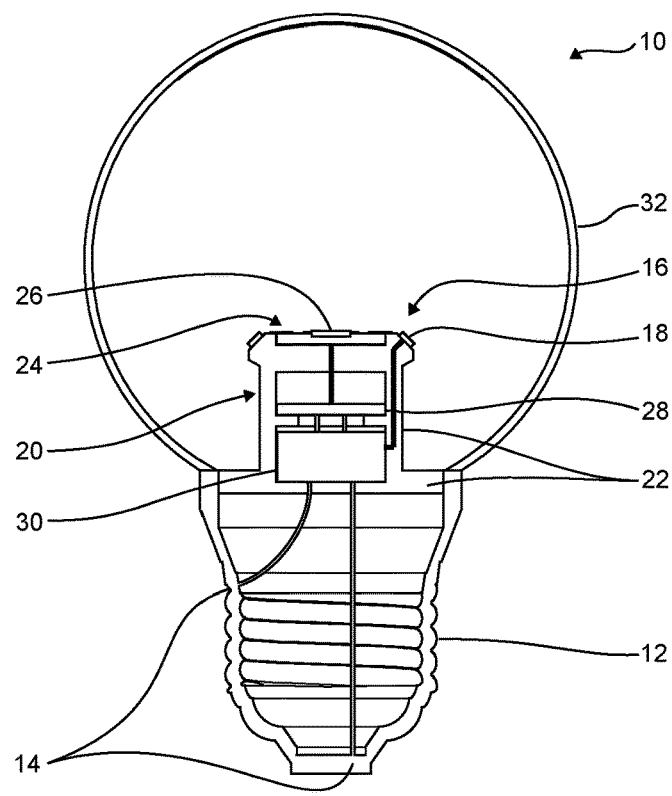
FIGS. 1a and 1b are schematic illustrations of a plane projection and a perspective view, respectively, of a cut through of a lamp and a detector according to an embodiment.
Figure 1B:
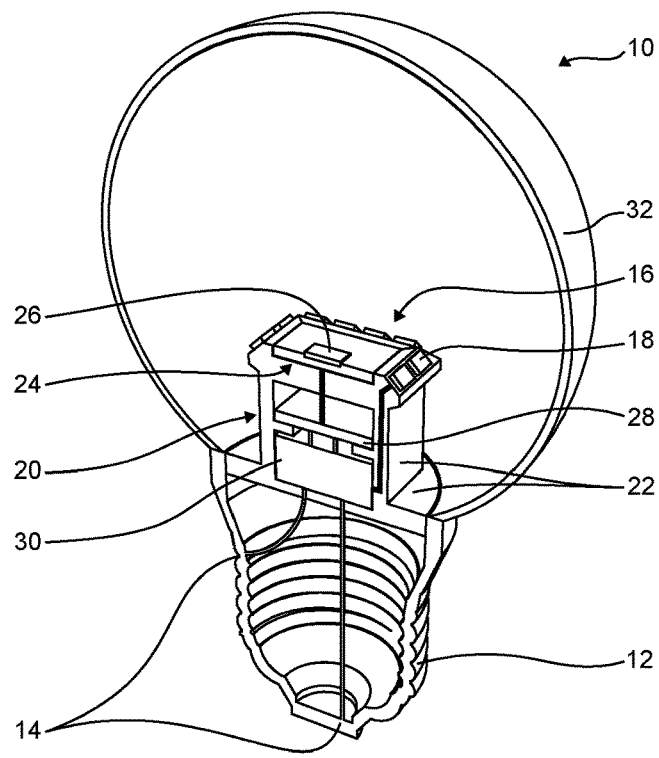

With reference to FIGS. 1a and 1b, a lamp 10 is illustrated having a base 12 that can fit in a socket of a light-fixture (not shown). In the shown embodiment, the base 12 is an Edison screw. In other embodiments, bases configured for other socket are used, such as bayonet mounts and Bi-pin connectors. The base 12 has an electric contact that can establish an electric connection with a socket. The lamp has a light emitter 16 in the form of several Light-Emitting Diodes (LEDs) 18. The diodes are directed outward so that they illuminate the surroundings of the lamp 10.

The lamp 10 also has a detector 20 with a support structure 22 that is connected to and supported by the base 12. A CW radar module 24 is supported by the support structure 22. The radar module 24 has an antenna 26 that is oriented to emit microwaves in direction away from the base 12. The radar module 24 radiate microwaves at maximum power in this direction and receives microwaves at maximum power gain from the opposite direction. The radar module 24 operates in the range 57 to 66 GHz. In alternative embodiments, the radar module 24 operates in the range 20 to 29 GHz, or in the range 118 to 127 GHz. For example, the radar module may be based on technologies disclosed in "Development of a 60 GHz radar for rear-end collision avoidance," Yamada, Y. et al., *Proceedings of the Intelligent Vehicles '94 Symposium.*

The LEDs 18 of the light-emitter 16 are oriented and positioned so that they form a pattern of varying brightness with a dark spot that indicates the direction pointing away from the base 12, thus also indicating the direction at which the radar module 24 radiate microwaves at maximum power.

The radar module 24 has a processor (not shown) and a non-volatile memory (not shown). Program code instructions are stored in the non-volatile memory that causes the processor to operate the radar module and generate data that correspond to an amplitude diagram indicating heart beats and/or breathing of a person upon which the microwaves are reflected. This way, the data indicates bodily functions of the person. The radar module 24 can operate in two modes. In the first mode, Doppler radar is used for determining the data, and in the second mode, frequency-modulated carrier-waves are used for determining the data.

The detector 20 has a wireless communication circuit 28 that is supported by the support structure 22. The circuit 28 is operationally connected to the radar module 24 and can transmit a signal indicating data determined by the radar module 24 over a Wireless Local Area Network (WLAN). In alternative embodiments, the radar module 24 and can transmit a signal over a Bluetooth connection.

The detector 20 has a power converter 30 that is coupled to the electric contact 14. The power converter 30 is coupled to the light-emitter 16 and the detector 20 and supplies these components with electrical power. The power converter is configured to receive mains electricity of 230 V AC at 50 Hz. In alternative embodiments, it is configured to receive mains electricity of 120 V AC at 60 Hz, or direct current electricity of 6V, 12 V or 24 V DC.

The lamp 10 has a bulb 32 of a translucent plastic material translucent to both optical light and microwaves that is connected to the base 12 and covers the light emitter 16, the detector 20, the wireless communication circuit 28, and the and power converter 30.

Figure 2:
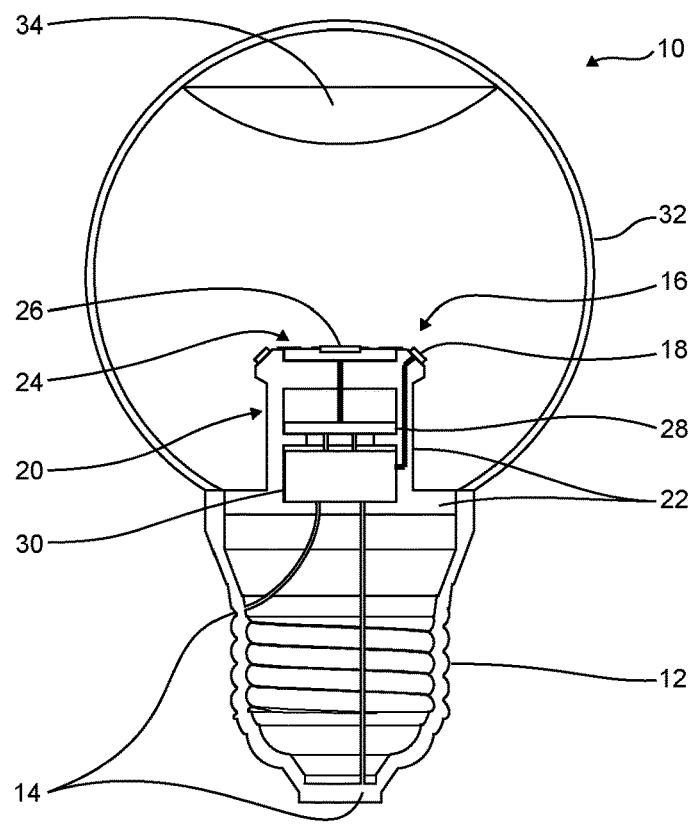
FIG. 2 is a schematic illustration of a plane projection of a cut through of a lamp and a detector according to an embodiment.

Another embodiment is shown in FIG. 2. Features having the same general function as in the embodiment described in relation to FIGS. 1a and 1b have been given the same number indexing. In addition to the common features, the embodiment also has a microwave lens 34 of a plastic material that is attached to the bulb 32. The material is translucent to both optical light and microwaves. The lens 34 is located at a distance from the radar module 24 and centered on the antenna 26 of the radar module 24. Microwaves emitted by the antenna 26 of the radar module 24 are collimated by the lens. The lens also focuses reflected microwaves on the antenna 26. Light from the light-emitter 16 can pass through the lens 34 and the bulb 32 and illuminate the surroundings of the lamp 10.

Figure 3:
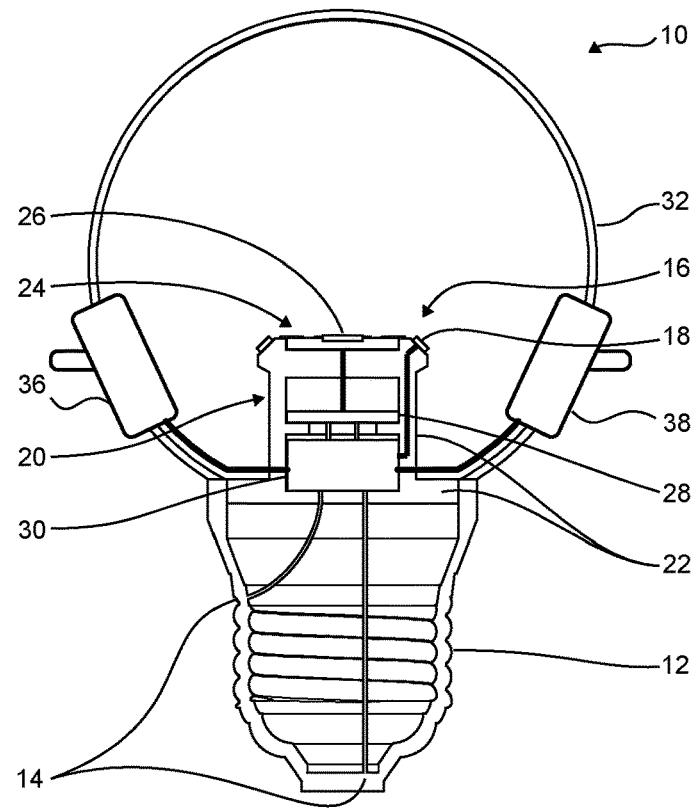
FIG. 3 is a schematic illustration of a plane projection of a cut through of a lamp and a detector according to an embodiment.

Another embodiment is shown in FIG. 3. Also here, features having the same general function as in the embodiment described in relation to FIGS. 1a and 1b have been given the same number indexing. In this embodiment, the lamp 10 has a first manual switch 36 connected to the power converter 30 by which the radar module can be switched on and off. The lamp 10 also has a second manual switch 38 connected to the power converter 30 by which the light emitter 16 can be switched on and off.

Figure 4A:
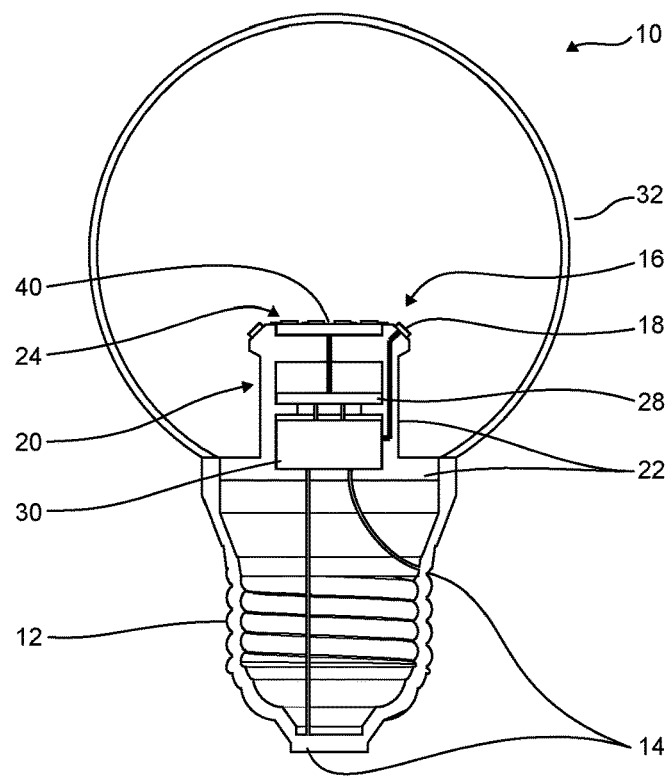
FIGS. 4a and 4b are schematic illustrations of a plane projection and a perspective view, respectively, of a cut through of a lamp and a detector according to an embodiment.
Figure 4B:
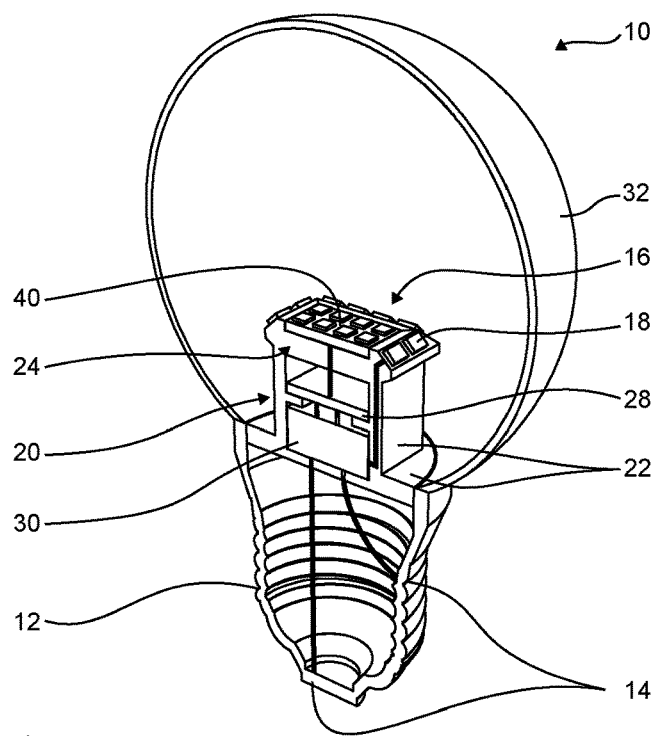

With reference to FIGS. 4a and 4b, another embodiment of a lamp 10 is illustrated. Features in common with or relating to the features of the embodiment described in relation to FIGS. 1a and 1b have been given the same number indexing. In this embodiment, the radar module 24 has a phased array antenna 40. The array antenna 40 is setup to reinforce a microwave radiation pattern in a specific direction, and the directions can be changed by commands received via the wireless communication circuit 28.

Figure 5A:
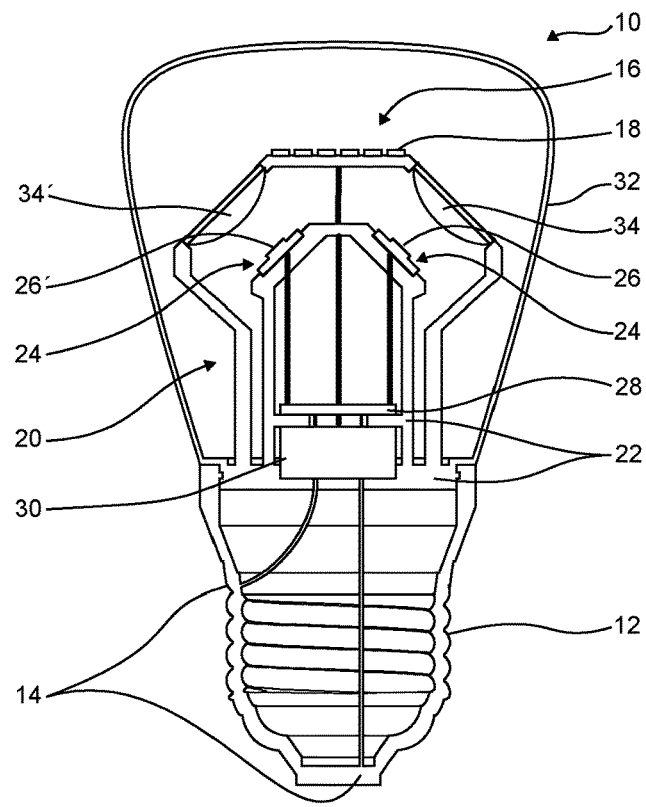
FIGS. 5a and 5b are schematic illustrations of a plane projection and a perspective view, respectively, of a cut through of a lamp and a detector according to an embodiment.
Figure 5B:
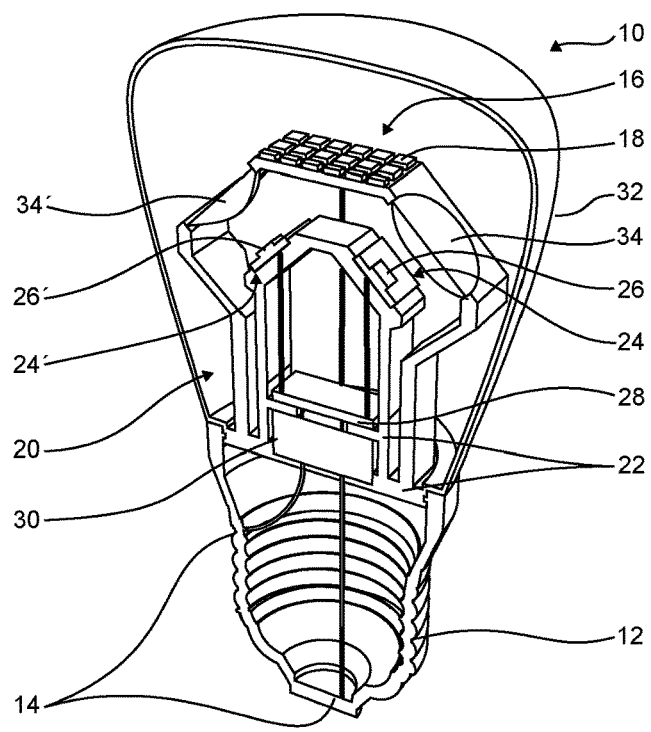

Another embodiment is shown in FIGS. 5a and 5b. The number indexing of features in common with the embodiment described in relation to FIGS. 1a and 1b has been maintained. The radar module 24 has two antennas 26 and 26'. Each antenna 26 and 26' is oriented to that the direction in which it radiate microwaves at maximum power is at an angle to the symmetry axis of the base 12. Lenses 34 and 34' are supported by the support structure 22 and positioned so that the microwaves are collimated for respective antennas 26 and 26'. Thus, the lenses 34 and 34' are fixed relative to the radar module 24 and the support structure 22.

The support structure 22 is rotationally coupled to the base 12 so that it can rotate around an axis extending along the symmetry axis of the base 12. The bulb 32 is attached to the support structure 22, and the support structure 22 can be rotated with respect to the base 12 by gripping and twisting the bulb 32. This way, the orientation of the radar module, and the points of detection in the surroundings, can be changed.

Figure 6:
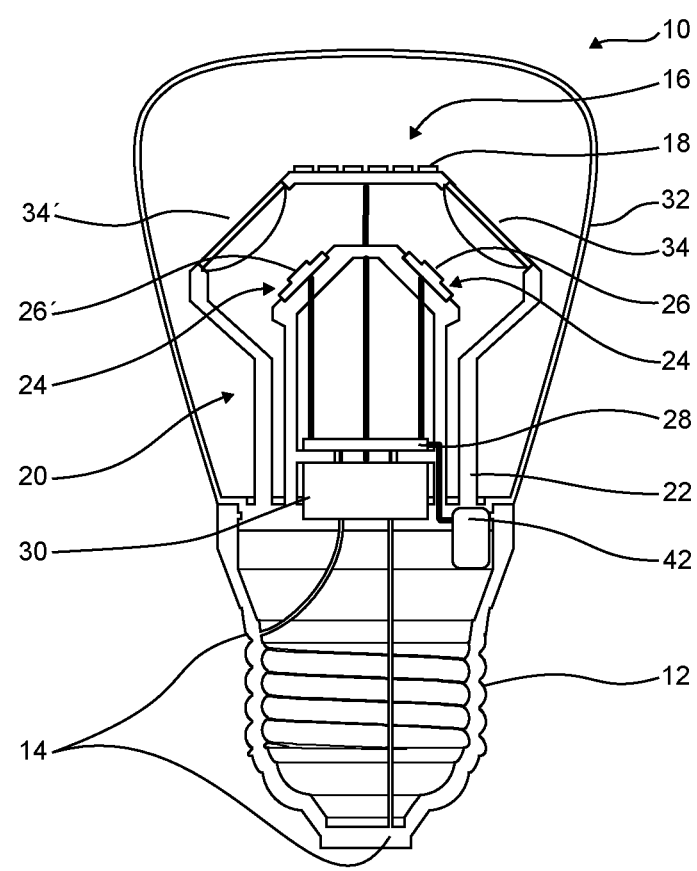
FIG. 6 is a schematic illustration of a plane projection of a cut through of a lamp and a detector according to an embodiment.

Another embodiment is shown in FIG. 6. This embodiment shares features with the embodiment described in relation to FIGS. 5a and 5b. Additionally, a first actuator 42 in the form of an electric motor controlled by the wireless communication circuit 28 is supported by the support structure 22. The first actuator 42 is operationally connected with the base 12 by way of sprockets (not shown), and can rotate the support structure 22 with respect to the base on commands received by the wireless communication circuit 28. The support structure 22 can also be rotated manually with respect to the base 12 by gripping and twisting the bulb 32.

Figure 7A:
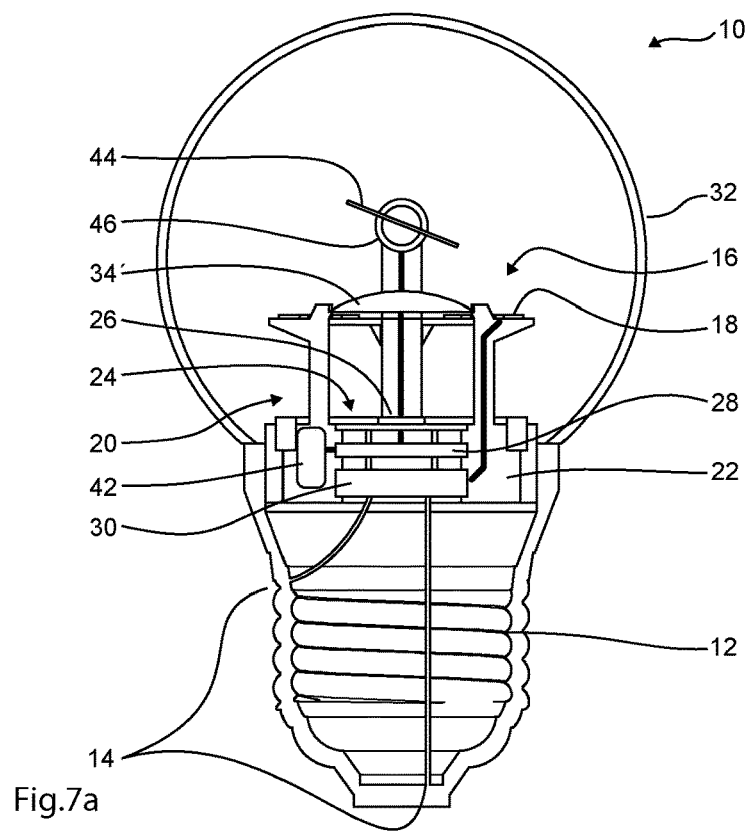
FIGS. 7a and 7b are schematic illustrations of a plane projection and a perspective view, respectively, of a cut through of a lamp and a detector according to an embodiment.
Figure 7B:
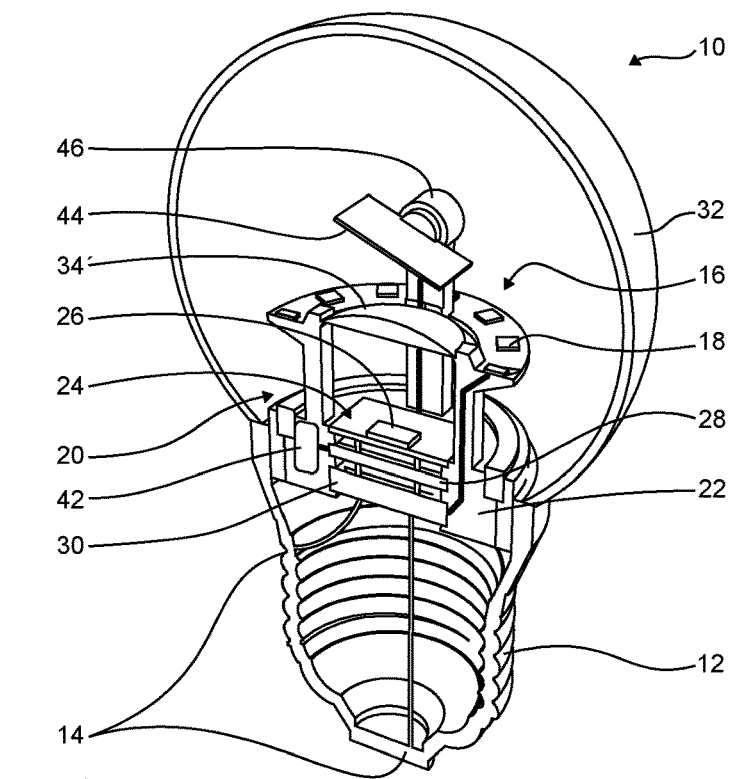

With reference to FIGS. 7a and 7b, another embodiment of a lamp 10 is illustrated. The number indexing of features in common with the other embodiments described above have been maintained. The detector 20 has a reflector 44 in the form of a planar sheet of metal.

The reflector 44 is positioned so that it can reflect and change the direction of microwaves emitted from the radar module 24. The reflector 44 is connected to a second actuator 46 that can tilt the reflector 44 so that the direction of the microwaves changes. The second actuator 46 is coupled to the wireless communication circuit 28, by which it can be remotely controlled. The detector 20 also has a lens 34' positioned between the radar module 24 and the reflector 44 so that the microwaves are collimated before they reach the reflector 44.

The support structure 22 is rotationally coupled to the base 12 so that it can rotate around an axis extending along the symmetry axis of the base 12, as in the embodiments described in relation to FIGS. 5a and 5b. Additionally, it also has a first actuator 42 similar to the one in the embodiment described in relation to FIG. 6. This way, the direction of the microwaves can cover a large portion of the surroundings by remote control via wireless communication circuit 28. The embodiment of FIGS. 7a and 7b differs in that the bulb 32 is attached to the base 12, which means that the orientation cannot be changed manually. In one embodiment, the bulb 34 is releasably attached to the base 12 and can be removed so that the tilt of the reflector 44 can be changed manually.

Figure 8A:
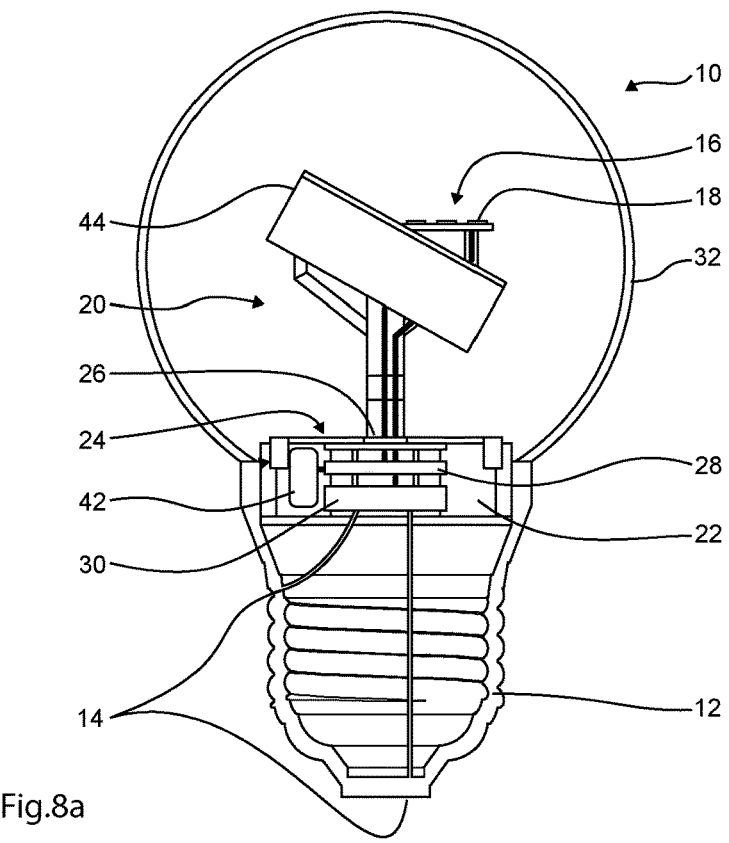
FIGS. 8a and 8b are schematic illustrations of a plane projection and a perspective view, respectively, of a cut through of a lamp and a detector according to an embodiment.
Figure 8B:
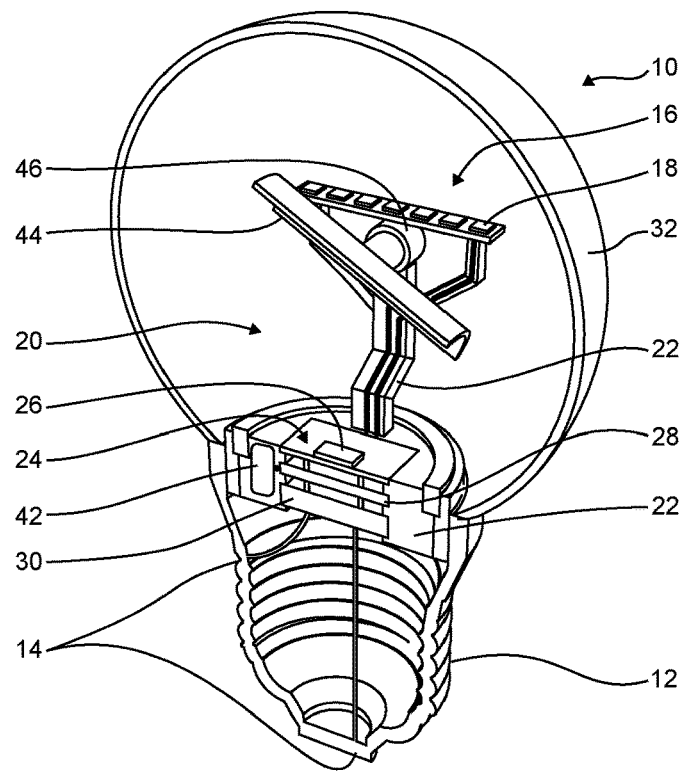

Another embodiment is shown in FIGS. 8a and 8b. This embodiment shares features with the embodiment described in relation to FIGS. 7a and 5b, and the number indexing of features has been maintained. This embodiment differs in that it has no lens positioned between the reflector 44 and the radar module 20. Instead, the reflector 44 is a portion of a circular cylinder that collimates the microwaves.

Figure 9A:
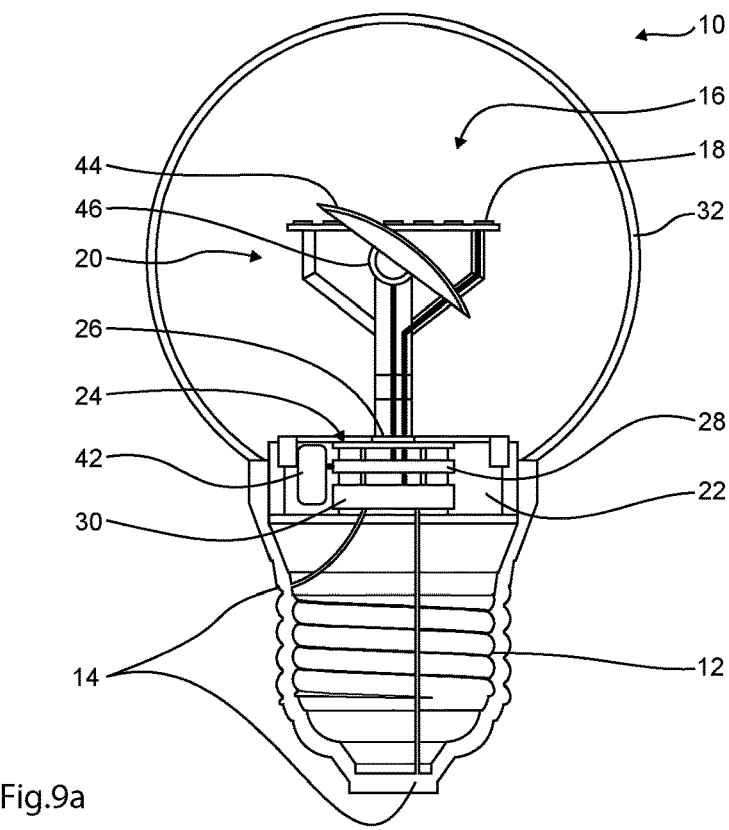
FIGS. 9a and 9b are schematic illustrations of a plane projection and a perspective view, respectively, of a cut through of a lamp and a detector according to an embodiment.
Figure 9B:
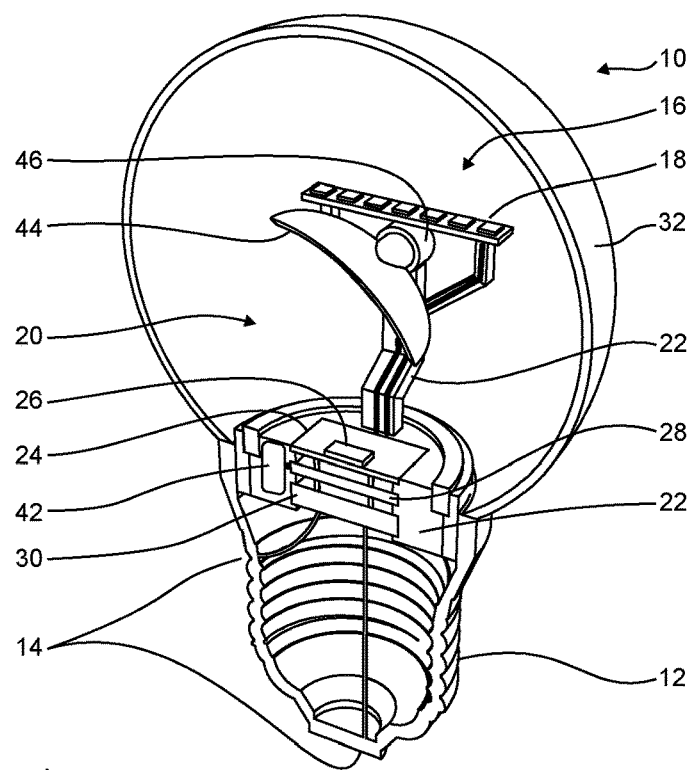

Yet another embodiment is shown in FIGS. 9a and 9b. This embodiment shares features with the embodiment described in relation to FIGS. 8a and 8b, and the number indexing of features has been maintained. This embodiment differs in that it that the reflector 44 is a portion of a paraboloid.

In alternative embodiments to the above embodiments of a lamp 10, the light emitter 16 can be removed, thus converting the lamp 10 to a detector 20.

Figure 10A:
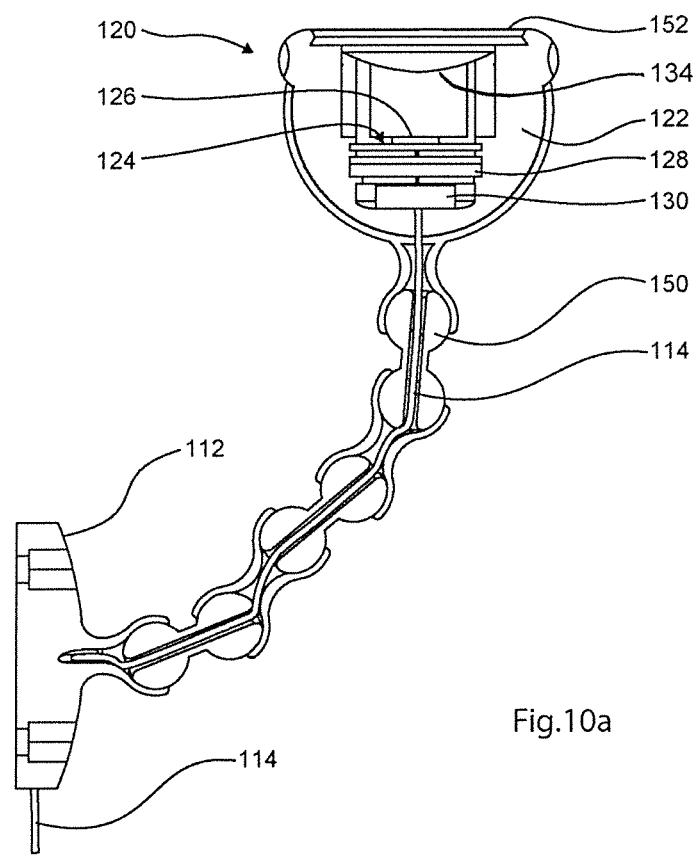
FIGS. 10a and 10b are schematic illustrations of a plane projection and a perspective view, respectively, of a cut through of a lamp and a detector according to an embodiment
Figure 10B:
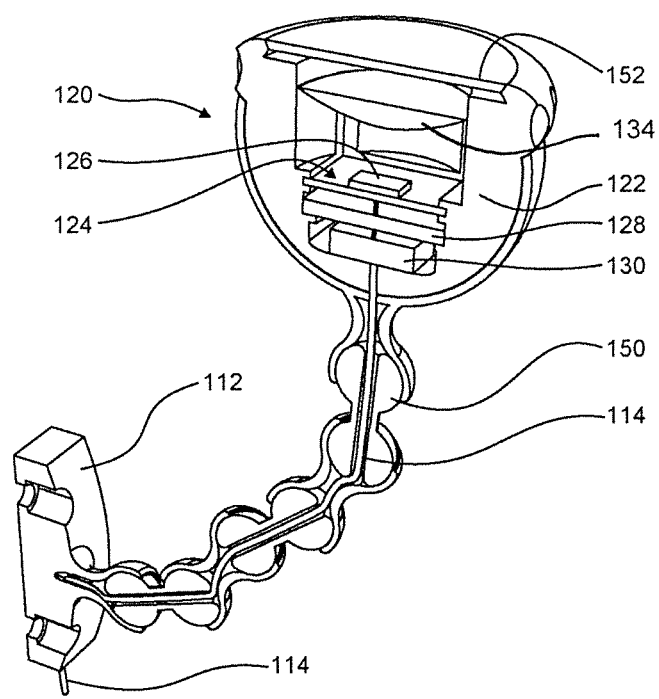

With reference to FIGS. 10a and 10b, a detector 120 is illustrated having a base 112 that can be mounted on the wall or in the ceiling. The detector 120 has a support structure 122 that is connected to and supported by the base 112. A CW radar module 124 is supported by the support structure 122. The radar module 124 has an antenna 126 that can radiate microwaves at maximum power in a specific direction and receives microwaves at maximum power gain from the opposite direction. The radar module 124 operates in the range 57 to 66 GHz. In alternative embodiments, the radar module 124 operates in the range 20 to 29 GHz, or in the range 118 to 127 GHz. For example, the radar module may comprise a.

The radar module 124 has a processor (not shown) and a non-volatile memory (not shown). Program code instructions are stored in the non-volatile memory that causes the processor to operate the radar module 124 and generate data that correspond to an amplitude diagram indicating heart beats and/or breathing of a person upon which the microwaves are reflected. This way, the data indicates bodily functions of the person. The radar module 124 can operate in two modes. In the first mode, Doppler radar is used for determining the data, and in the second mode, frequency-modulated carrier-waves are used for determining the data.

The detector 120 has a wireless communication circuit 128 that is supported by the support structure 122. The circuit 128 is operationally connected to the radar module 124 and can transmit a signal indicating data determined by the radar module 124 over a Wireless Local Area Network (WLAN).

The detector 120 has a power converter 130 that is coupled to an electric contact 114. The power converter 130 is coupled to and supplies the detector 120 with electrical power. The power converter is configured to receive mains electricity of 230 V AC at 50 Hz. In alternative embodiments, it is configured to receive mains electricity of 120 V AC at 60 Hz, or direct current electricity of 6V, 12 V or 24 V DC.

A lens 134 of a plastic material is supported by and fixed relative to the support structure 122. The lens 134 is located at a distance from the radar module 124 and centered on the antenna 126 of the radar module 124. Microwaves emitted by the antenna 126 are collimated by the lens 134, and the lens also focuses reflected microwaves on the antenna 126. The lens is protected by a plastic cover 152 transparent to the microwaves.

The support structure 122 is attached to the base 112 via an articulated arm 150. This allows for the orientation of the support structure 112, and the direction of the emitted microwaved, to be manually adjusted.

Figure 11:
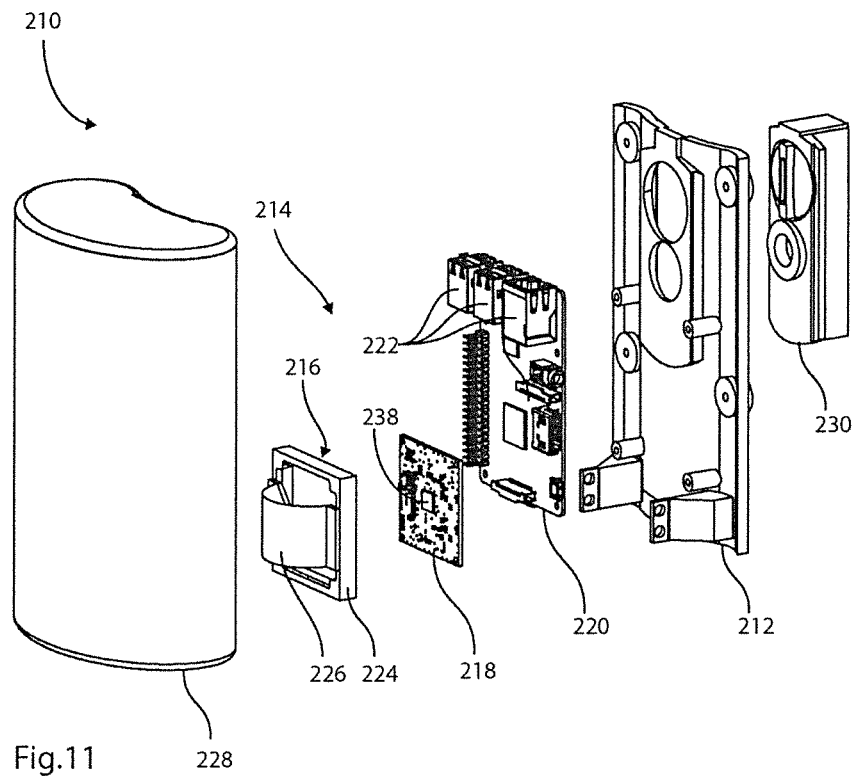
FIG. 11 is a perspective and exploded view of an embodiment of a detector.

FIG. 11 illustrates the components of an embodiment of a detector 210 for indicating or monitoring bodily functions of a person. The detector 210 has a Continuous-Wave (CW) radar module 214 and a collimator 216. The radar module 214 has an antenna module 238 on a printed circuit board 218 operationally connected to a microcontroller board 220. The operation of the antenna module 238 is controlled by the microcontroller board 220. The microcontroller board 220 has connections 222 for external communication and power supply.

The collimator 216 has a frame 224 into which the printed circuit board 218 is fitted. The collimator 216 further has a refractive body 226 positioned in front of the antenna module 238. The refractive body 226 is further described below in relation to FIGS. 12 and 13a-e.

The collimator 216 with the fitted printed circuit board 218 is stacked on the microcontroller board 220, which in turn is stacked on a back plate 212. Thus, the back plate 212 and frame 224 of the collimator 216 jointly constitutes a support structure for the radar module 214.

The detector 210 has a plastic cover 228 connectable to the back plate 212 and that is transparent to microwaves and covers the collimator 216 and the radar module 214. The detector further has a connector 230 similar to connectors for rail-support commonly used for spotlights. The connector 230 is releasably attached to the back plate 212 and can form an electric connection to an electrical conduit of a supporting rail, by which the radar module 214 can be supplied with electric power.

Figure 12:
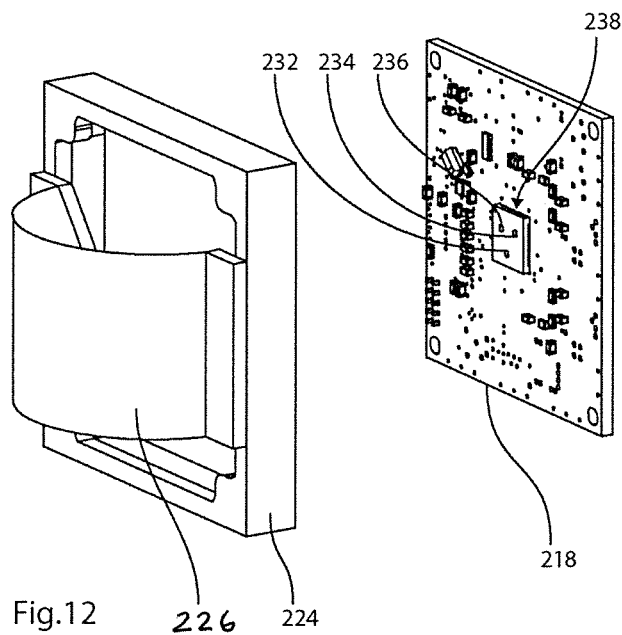
FIG. 12 is a perspective view of the radar module and collimator of the embodiment described in relation to FIG. 11, FIGS. 13a-e are different views of the refractive body of the collimator of the embodiment described in relation to FIG. 11.

The collimator 216 and the printed circuit board 218 with the antenna module 238 are shown in greater detail in FIG. 12. The antenna module 238 has an emitting antenna 232, a first receiving antenna 234, and a second receiving antenna 236. The refractive body 226 of the collimator 216 has the shape of a portion of a ring, more precisely a half-ring, and is centered over the antenna module 238 and oriented such that it is aligned with the first receiving antenna 234 and the second receiving antenna 236. The refractive body 226 is composed of ABS, which is refractive to microwaves. Other polymers that are refractive to microwaves can be used in alternative embodiments.

Figure 13A:
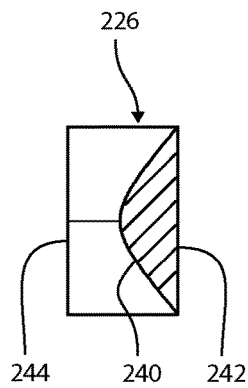
Figure 13B:
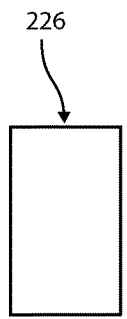
Figure 13C:
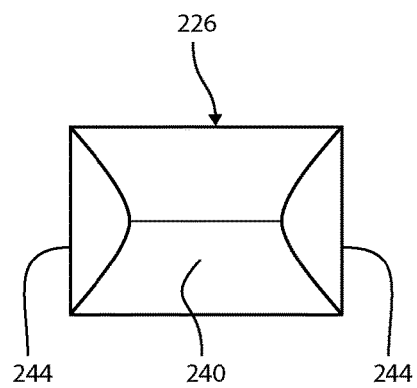
Figure 13E:
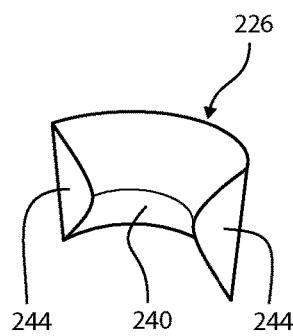
Figure 13D:
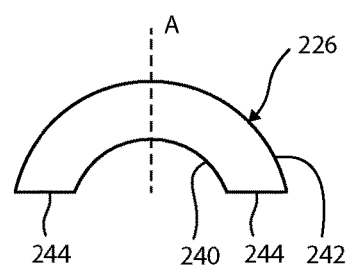

Details of the refractive body 226 are shown in FIGS. 13a-e. A perspective view is shown in FIG. 13e, side views are shown in FIGS. 13b and 13d, a bottom view is shown in FIG. 13c, and a cross-section along the line A indicated in FIG. 13d is shown in FIG. 13a. The refractive body 226 is formed like a portion of a ring with an inner side 240, an outer side 242, and two ends 244, such that it constitutes a portion of a ring corresponding to an arc subtending an angle of 180°, or a half-ring.

Figure 14:
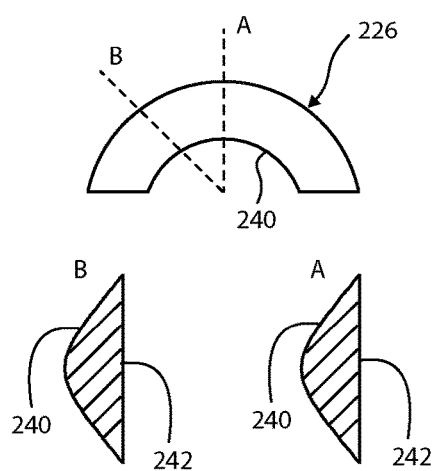
FIG. 14 is a side view and two different cross-sections of the refractive body of the collimator of the embodiment described in relation to FIG. 11.

Two different cross-sections of the refractive body 226 are illustrated in FIG. 14. The cross-sections are indicated by the lines A and B in the side view of the refractive body 226. Thus, the cross-sections are transverse or radial to the portion of the ring constituting the refractive body 226. The inner side 240 of each transverse cross-section facing the antenna module 238 is convex and the outer side 242 of each transverse cross-section facing away from the antenna module 238 is straight. Each transverse cross-section between the ends of the refractive body 226 has the same radius of curvature on the convex inner side 240.

Figure 15:
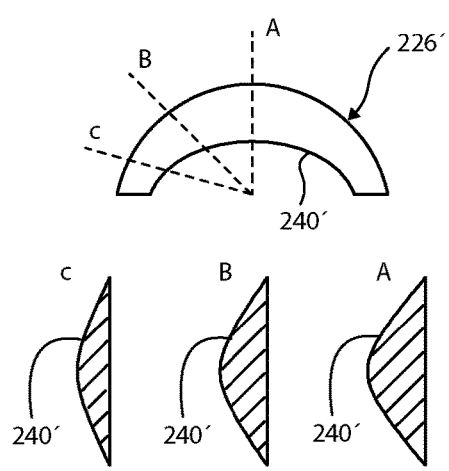
FIG. 15 is a side view and three different cross-sections of the refractive body of a collimator of an alternative embodiment.

In an alternative embodiment illustrated in FIG. 15, the convex inner side 240' has a curvature that varies along the portion of the ring constituting the refractive body 226'. Three different cross-sections are indicated by the lines A, B, and C. The curvature of the convex inner side 240' is the greatest at the middle or center of the portion of the ring and gradually decreases towards its ends 244'.

Figure 16:
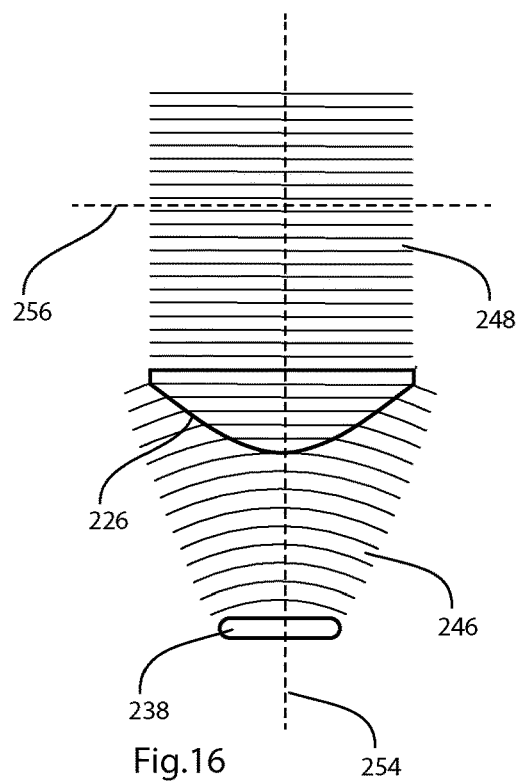
FIG. 16 is a schematic illustration of the function of the refractive body of the collimator of the embodiment described in relation to FIG. 11, and FIGS. 17a-c are different views of an embodiment of a detector system.

The functions of the refractive body 226 is schematically illustrated in FIG. 16 showing a cross-section of the refractive body 226, which corresponds to the cross-section indicated by A in FIG. 13*d*. The antenna module 238 emits microwaves that are indicated by the expanding wave fronts 246. The microwaves enter the refractive body and form parallel wave fronts 248 that are maintained when the microwaves continue from the refractive body 226. Thus, the microwaves emitted from the antenna module 238 are collimated and the spread of the microwaves is reduced towards a plane 254 with a normal 256 indicated by the dashed line.

Figure 17A:
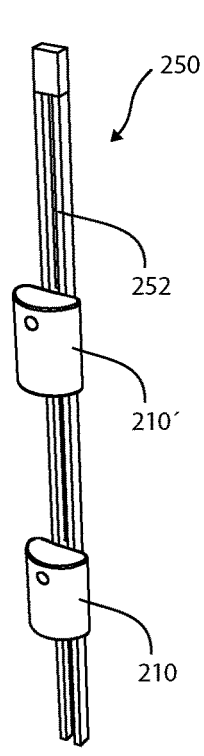
Figure 17B:
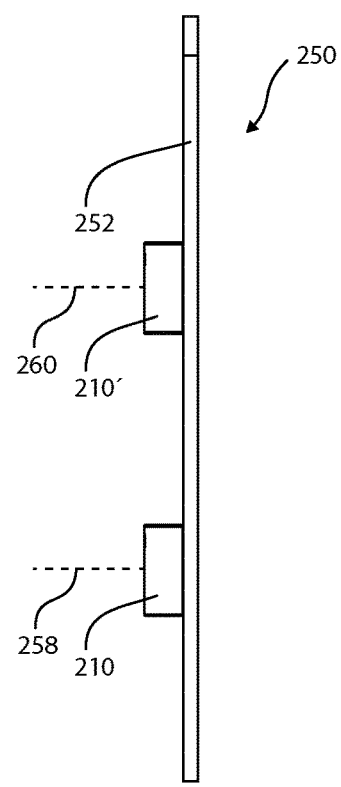
Figure 17C:
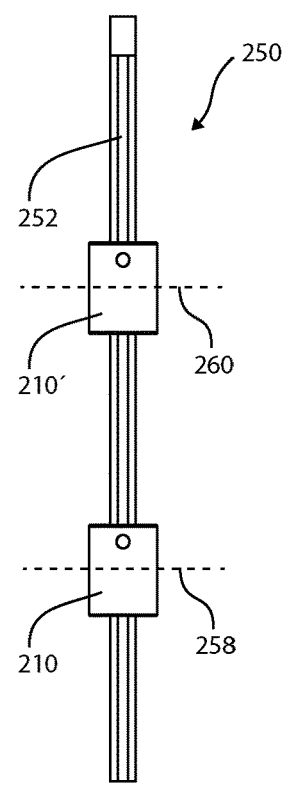

An embodiment of a detector system for indicating bodily functions of a person in a room is illustrated in FIGS. 16*a-c*. The detector system has a first detector 210 and a second detector 210'. Both detectors have the same features as the detector 210 described above in relation to FIG. 11. Each of the detectors 210 and 210' is slidably attached by a respective connector 230 to a rail 252 constituting a detector support that supports the first detector 210 and the second detector 210'. Thus, the positions of the first detector 210 and the second detector 210" are adjustable along the rail. The rail is similar to the rails commonly used for supporting spotlights, The rail 252 is attached in a vertical orientation on the wall of a room by screws engaging the wall through holes in the rail (not shown). This way, the first detector 210 and the second detector 210" are positioned at different heights or levels in the room. The first detector 210 and the second detector 210' are oriented such that they collimate the microwaves in the vertical direction, or towards a first horizontal plane 258 and a second horizontal plane 260, as indicated in FIGS. 17*b* and 17*c*. They detectors 210 and 210" are further oriented such that their respective antenna modules 238 face the same direction.

The rail 252 is positioned with its lower end at floor level, and it has a length such that the position of the first detector 210 can be adjusted between 0.1 m and 1 m from the floor of the room and the position of the second detector can be adjusted between 1 m and 2 m from the floor of the room.

The rail 252 has an electrical conduit (not shown) that connects to the connector 230 of each detector 210 and 210' such that their respective radar modules 214 can be supplied with electric power via the rail 252.

In an alternative embodiment, the rail 252 is supported in a vertical orientation by a base or stand attached at its lower end and resting on the floor of the room.

From the description above follows that, although various embodiments of the invention have been described and shown, the invention is not restricted thereto, but may also be embodied in other ways within the scope of the subject-matter defined in the summary and the following claims.

ITEM LIST

10 lamp
12 base
14 electric contact
16 light emitter
18 LEDs
20 detector
22 support structure
24 radar module
26 antenna
28 wireless communication circuit
30 power converter
32 bulb
34 lens
36 first manual switch
38 second manual switch
40 phased array antenna
42 first actuator
44 reflector
46 second actuator
112 base
114 electric contact
120 detector
122 support structure
124 radar module
126 antenna
128 wireless communication circuit
130 power converter
134 lens
150 articulated arm
152 cover
210 detector
212 back plate
214 radar module
216 collimator
218 printed circuit board
220 microcontroller board
222 connections for communication and power supply
224 frame
226 refractive body
228 cover
230 connector
232 emitting antenna
234 first receiving antenna
236 second receiving antenna
238 antenna module
240 inner side
242 outer side
244 ends
246 expanding wave fronts
248 parallel eave fronts
250 detector system
252 rail
254 plane
256 normal
258 first horizontal plane
260 second horizontal plane

The invention claimed is:

1. A detector for indicating bodily functions of a person in the surroundings of the detector, wherein the detector comprises:
   a Continuous-Wave (CW) radar module configured to emit microwaves and receive reflected microwaves, wherein the radar module is configured to determine data indicating bodily functions from microwaves reflected from the person; and
   a collimator configured for collimating the emitted microwaves in one spatial direction toward a single horizontal plane;
   wherein the radar module comprises an antenna module operable for emitting microwaves and receiving microwaves, wherein the collimator comprises a refractive body that is refractive to the microwaves, wherein the refractive body constitutes a portion of a ring having an inner side and an outer side, and wherein the refractive body is positioned in front of the antenna module with its inner side facing the antenna module.

2. The detector according to claim 1, wherein the refractive body constituting a portion of a ring has a transverse cross-section with a convex inner side facing the antenna module.

3. The detector according to claim 1, wherein the refractive body constituting a portion of a ring has a transverse cross-section with a straight outer side facing away from the antenna module.

4. The detector according to claim 1, wherein the antenna module comprises first and second receiving antennas configured for intercepting microwaves that have been reflected in the surroundings of the detector, wherein the first receiving antenna is spaced apart from the second receiving antenna, and wherein the refractive body constituting a portion of a ring is aligned with the first receiving antenna and the second receiving antenna.

5. A detector system for indicating bodily functions of a person in a room, wherein the detector system comprises:
(a) a first detector, comprising:
(i) a first Continuous-Wave (CW) radar module configured to emit microwaves and receive reflected microwaves, wherein the first radar module is configured to determine data indicating bodily functions from microwaves reflected from the person; and
(ii) a first collimator configured for collimating the emitted microwaves from the first radar module in one spatial direction toward a first horizontal plane at a first vertical height, wherein the first collimator comprises a first refractive body that is refractive to the microwaves; and
(b) a second detector, comprising:
(i) a second Continuous-Wave (CW) radar module configured to emit microwaves and receive reflected microwaves, wherein the second radar module is configured to determine data indicating bodily functions from microwaves reflected from the person; and
(ii) a second collimator configured for collimating the emitted microwaves from the second radar module in the one spatial direction toward a second horizontal plane at a second vertical height, wherein the second collimator comprises a second refractive body that is refractive to the microwaves;
wherein the first and second collimators are configured to collimate the emitted microwaves from the first radar module and the second radar module, respectively, toward the first plane and the second plane, respectively, wherein the first plane and the second plane are parallel.

6. The detector system according to claim 5, wherein the first collimator and the second collimator are oriented to collimate the emitted microwaves from the first and second radar modules toward the first and second horizontal planes, respectively, in a vertical direction.

7. The detector system to claim 5, wherein the first detector and the second detector are positioned at different heights in the room.

8. The detector system according to claim 5, wherein the first detector includes a first antenna module and the second detector includes a second antenna module, wherein the first and second detectors are aligned in a vertical direction, and wherein the first antenna module and the second antenna module face the same direction.

9. The detector system according to claim 5, further comprising:
a detector support including a vertical rail supporting the first and second detectors, wherein the vertical positions of the first and second detectors are adjustable along the rail.

10. A detector for indicating bodily functions of a person in the surroundings of the detector, wherein the detector comprises:
a Continuous-Wave (CW) radar module configured to emit microwaves and receive reflected microwaves, wherein the radar module is configured to determine data indicating bodily functions from microwaves reflected from the person; and
a collimator configured for collimating the emitted microwaves in one spatial direction toward a horizontal plane;
wherein the radar module comprises an antenna module operable for emitting microwaves and receiving microwaves, and wherein the collimator comprises a refractive body that is refractive to the microwaves; and
wherein the refractive body constitutes a portion of a ring having an inner side and an outer side, and wherein the refractive body is positioned in front of the antenna module with its inner side facing the antenna module.

11. The detector according to claim 10, wherein the refractive body constituting a portion of a ring has a transverse cross-section with a convex inner side facing the antenna module.

12. The detector according to claim 10, wherein the refractive body constituting a portion of a ring has a transverse cross-section with a straight outer side facing away from the antenna module.

13. The detector according to claim 10, wherein the antenna module comprises first and second receiving antennas configured for intercepting microwaves that have been reflected in the surroundings of the detector, wherein the first receiving antenna is spaced apart from the second receiving antenna, and wherein the refractive body constituting a portion of a ring is aligned with the first receiving antenna and the second receiving antenna.

* * * * *